United States Patent [19]
Lum et al.

[11] Patent Number: 5,789,416
[45] Date of Patent: Aug. 4, 1998

[54] N[6] MONO HETEROCYCLIC SUBSTITUTED ADENOSINE DERIVATIVES

[75] Inventors: Robert T. Lum, Palo Alto; Jürg R. Pfister, Los Altos; Steven R. Schow, Redwood City, all of Calif.; Michael M. Wick, Chestnut Hill, Mass.; Marek G. Nelson, Sunol; George F. Schreiner, Los Altos Hills, both of Calif.

[73] Assignee: CV Therapeutics, Palo Alto, Calif.

[21] Appl. No.: 702,234

[22] Filed: Aug. 27, 1996

[51] Int. Cl.[6] .................. A61K 31/70; C07D 487/04
[52] U.S. Cl. .................. 514/261; 514/266; 544/262; 544/264
[58] Field of Search .................. 544/262, 264; 514/261, 266

[56] References Cited

U.S. PATENT DOCUMENTS

| | | | |
|---|---|---|---|
| 3,998,953 | 12/1976 | Konz et al. | 424/253 |
| 4,364,922 | 12/1982 | Berne et al. | 424/9 |
| 4,713,455 | 12/1987 | Furrer et al. | 544/267 |
| 4,954,504 | 9/1990 | Chen et al. | 514/265 |
| 4,980,379 | 12/1990 | Belardinelli et al. | 514/821 |
| 5,288,721 | 2/1994 | Klein et al. | 514/263 |
| 5,446,046 | 8/1995 | Belardinelli et al. | 514/263 |

FOREIGN PATENT DOCUMENTS

| | | |
|---|---|---|
| 0181109A2 | 10/1984 | European Pat. Off. |
| 0374808A2 | 12/1989 | European Pat. Off. |
| 0415456A2 | 3/1991 | European Pat. Off. |
| 4205306A1 | 2/1992 | Germany |
| 9200297 | 6/1990 | WIPO |
| 9416702 | 1/1993 | WIPO |

OTHER PUBLICATIONS

L. Belardinelli, et al, *Drug Development Research*, 28, pp. 263–267 (1993).
L. Belardinelli, et al., *Pace*, vol. 14, pp. 1672–1680 (1991).
L. Belardinelli, et al, *Progress in Cardiovascular Disease*, vol. XXXII, No. 1 (Jul./Aug.) pp. 79–97 (1989).
L. Belardinelli, et al, Cardiac *Electrophysiology of Adenosine*, pp. 327–339 (1990).
R. Olsson, et al, *The American Physiological Society*, vol. 70, pp. 761–782 (1990).
R. Olsson, et al, The American Physiological Society, vol. 70, pp. 783–805 (1990).
R. Olsson, et al, *The American Physiological Society*, vol. 70, pp. 806–826 (1990).
R. Olsson, et al, The American Physiological Society, vol. 70, pp. 827–845 (1990).
K. Jacobson, et al, American Chemical Society, vol. 35, pp. 407–422 (1992).
Fleysher, *J. Med. Chem*, vol. 15, pp. 187–191 (1972).

*Primary Examiner*—Mukund J. Shah
*Assistant Examiner*—Pavanaram K. Sripada
*Attorney, Agent, or Firm*—McDonnell Boehnen Hulbert & Berghoff

[57] ABSTRACT

A substituted $N^6$-oxa, thia, thioxa and azacycloalkyl substituted adenosine derivative and a method for using the composition as an $A_1$ heart adenosine receptor.

14 Claims, 1 Drawing Sheet

$N^6$ MONO HETEROCYCLIC SUBSTITUTED ADENOSINE DERIVATIVES

BACKGROUND OF THE INVENTION

1. Field of Invention

This invention encompasses optimally substituted $N^6$-oxa, thia, thioxa and azacycloalkyl substituted adenosine derivatives that are selective adenosine type 1 receptor agonists, and as such, are potentially useful agents for the treatment cardiovascular diseases and central nervous system disorders.

2. Description of the Art

There are two subtypes of adenosine receptors in the heart: $A_1$ and $A_2$. Each subtype effects different physiological functions. Stimulation of the $A_1$ adenosine receptor induces two distinct physiological responses. The first is the inhibition of the stimulatory effects of catecholamine. This effect is mediated via the inhibition of cyclic AMP synthesis. The second effect mediated by $A_1$ receptors is the slowing of the heart rate and impulse propagation through the AV node. The effect is independent of cAMP metabolism and is associated with $A_1$ adenosine receptor activation of the inwardly rectifying K+ channel. This effect is unique to the $A_1$ receptor; there is no role for the $A_2$ receptor in modulating the function of this channel. Stimulation of the adenosine $A_1$ receptor accordingly shortens the duration and decreases the amplitude of the action potential of AV nodal cells and subsequently prolongs the refractory period of the cells. The consequence of these effects is to limit the number of impulses conducted from the atria to the ventricles. This forms the basis of the clinical utility of $A_1$ receptor agonists for the treatment of supraventricular tachycardias, including atrial fibrillation, atrial flutter, and AV nodal re-entrant tachycardia.

The clinical utility of $A_1$ agonists therefore would be in the treatment of acute and chronic disorders of heart rhythm, especially those diseases characterized by rapid heart rate where the rate is driven by abnormalities in the atria. The disorders include but are not limited to atrial fibrillation, supra ventricular tachycardia and atrial flutter. Exposure to $A_1$ agonists causes a reduction in the heart rate and a regularization of the abnormal rhythm thereby restoring improved hemodynamic blood flow.

$A_1$ agonists, through their ability to inhibit the catecholamine induced increase in cAMP, should have beneficial effects in the failing heart where increased sympathetic tone causing enhanced cAMP has been associated with increased likelihood of ventricular arrhythmias and sudden death.

SUMMARY OF THE INVENTION

An object of this invention is novel heterocyclic substituted adenosine derivatives.

Another object of this invention is novel heterocyclic substituted adenosine derivatives that are useful as $A_1$ receptor agonists.

Still another object of this invention is novel heterocyclic substituted adenosine derivatives that are useful for treating supraventricular tachycardias, including atrial fibrillation, atrial flutter, and AV nodal re-entrant tachycardia.

In one embodiment, this invention is a composition of matter having the formula:

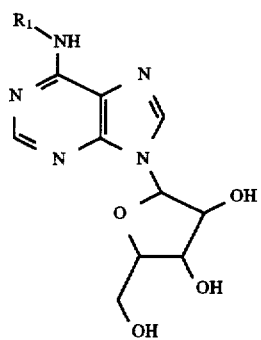

wherein $R_1$ is a monocyclic or polycyclic heterocyclic group containing from 3 to 15 atoms, at least one of which is N, O, S, P and wherein $R_1$ may be mono or polysubstituted with one or more compounds selected from the group consisting of halogen, oxo, hydroxyl, lower alkyl, substituted lower alky, alkoxy, aryl, acyl, aryloxy, carboxyl, substituted aryl, heterocycle, heteroaryl, substituted heteroaryl, cycloalkyl, substituted cycloalkyl, nitro, cyano and mixtures thereof wherein $R_1$ does not contain an epoxide group.

In another embodiment, this invention is a method for stimulating coronary activity in a mammal experiencing a cardiac electrical disorder that can be treated by stimulating an $A_1$ heart adenosine receptor by administering a therapeutically effective amount of the composition disclosed above to the mammal.

In still another embodiment, this invention is a pharmaceutical composition of matter comprising the composition of this invention and one or more pharmaceutical excipients.

DESCRIPTION OF THE CURRENT EMBODIMENT

Figure 1:
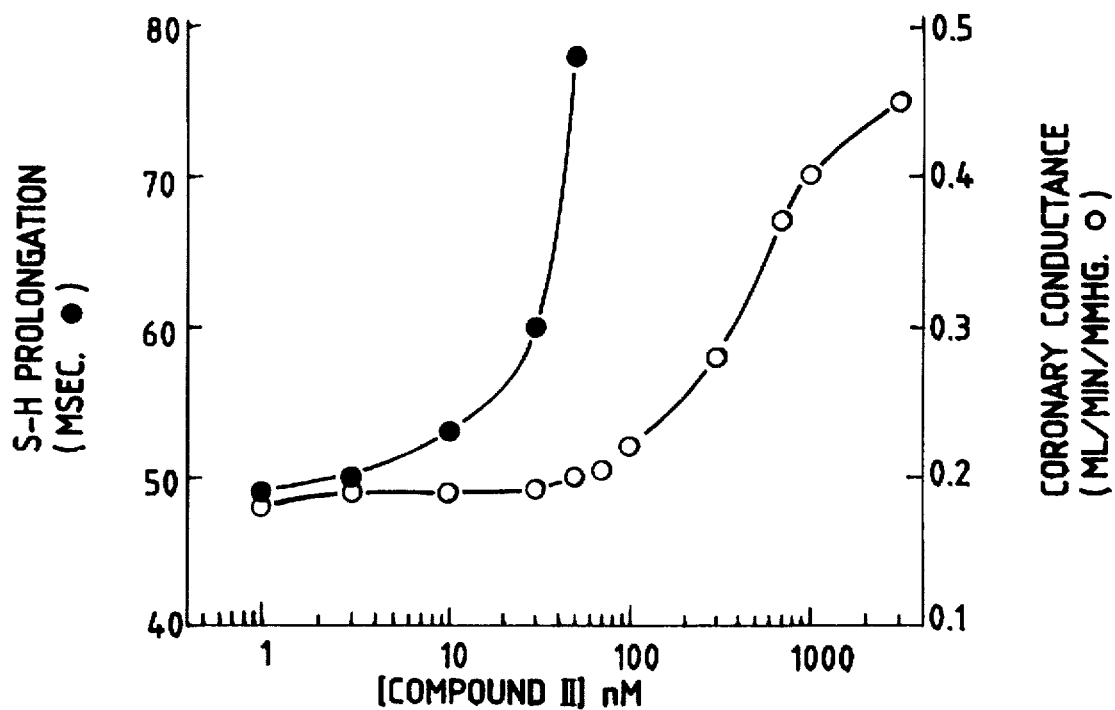
FIG. 1 is a plot of the effect of the concentration compound II of Example 2 on atrial AV nodal conductance for the $A_1$ adenosine receptor (–●–) and for the $A_2$ adenosine receptor (–○–).
Figure 2:
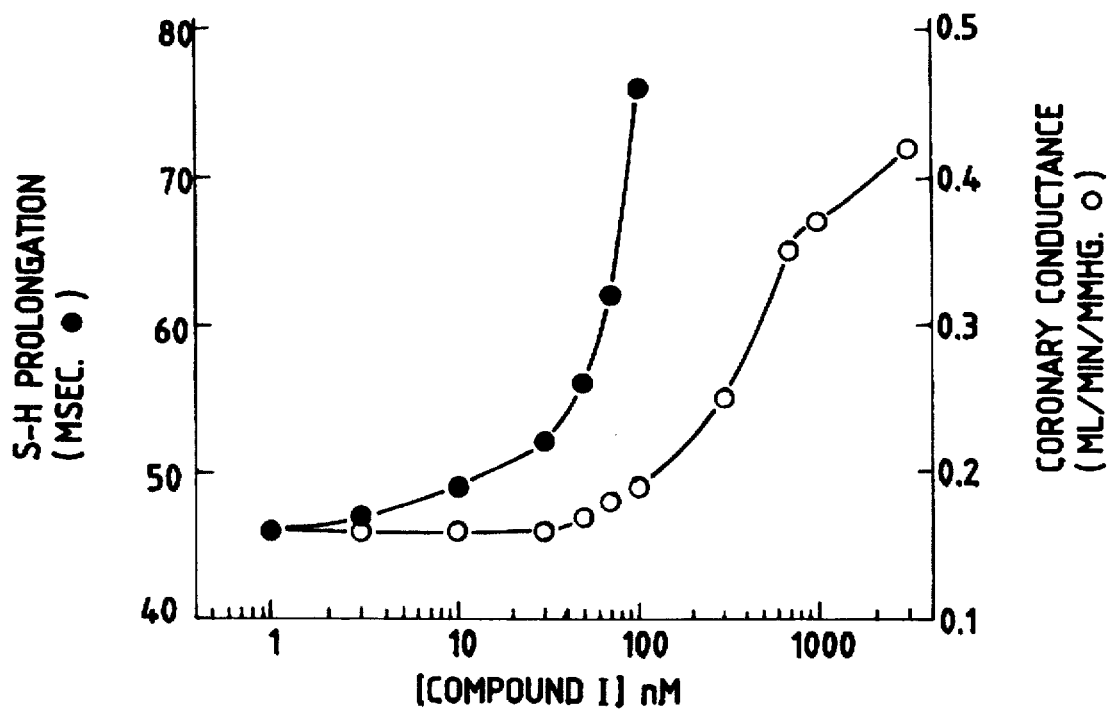
FIG. 2 is a plot of the effect of the concentration of compound I of Example 2 on atrial AV nodal conductance and specifically on the response of the $A_1$ adenosine receptor (–●–) and on the response of the $A_2$ adenosine receptor (–○–).

This invention comprises adenosine derivatives which are selective adenosine type 1 receptor agonists. The compositions are optimally substituted as described below.

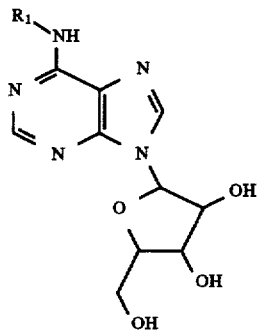

where:

$R_1$ is a cycloalkyl group, containing 3 to 15 atoms either monocyclic or polycyclic heterocyclic groups, at least one of which is a heteroatom selected from the group consisting of N, O, P, and S—(O)$_{0-2}$. R$_1$, in turn, may optionally be mono or polysubstituted with halogen, oxo, hydroxyl, lower alkyl, substituted lower alkyl, alkoxy, aryl, acyl, aryloxy, carboxyl, substituted aryl, heterocycle, heteroaryl, substituted heteroaryl, cycloalkyl, substituted cycloalkyl, nitro, and cyano. However, R$_1$ cannot contain an epoxy group.

R$_1$ is preferably a monocyclic, bicyclic, or tricyclic group containing from 3 to 15 atoms, at least one of which is selected from the group consisting of O or S—(O)$_{0-2}$ wherein R$_1$ may be mono or polysubstituted with one or more compounds selected from the group consisting of halogen, hydroxyl, lower alkyl, substituted lower alkyl, alkoxy, aryl, acyl, aryloxy, carboxyl, substituted aryl, heterocycle, heteroaryl, substituted heteroaryl, cycloalkyl, substituted cycloalkyl, nitro, cyano and mixtures thereof In a more preferred embodiment, R$_1$ is:

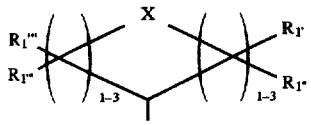

wherein R$_1$', R$_1$'', R$_1$''', and R$_1$'''' are individually selected from the group halogen, oxo, hydroxyl, lower alkyl substituted lower alky, alkoxy, aryl, acyl, aryloxy, carboxyl, substituted aryl, heterocycle, heteroaryl, substituted heteroaryl, cycloalkyl, substituted cycloalkyl, nitro, cyano and mixtures thereof and X is O, or S (—O)$_{0-2}$. Preferably, R$_1$', R$_1$'', R$_1$''', and R$_1$'''' are individually selected from the group H, lower alky, substituted lower alkyl, alkoxy, aryl, and substituted aryl. By "individually selected" it is meant that R$_1$', R$_1$'', R$_1$''', and R$_1$'''' may each be a different component, each may be the same component, e.g., hydrogen, or some of the components may be the same and some different. It is most preferred that when R$_1$ is the composition set forth above, that R$_1$', R$_1$'', R$_1$''', and R$_1$'''' are individually selected from the group H, lower alkyl, and substituted lower alkyl. R$_1$''' and R$_1$'''' may also be a single oxygen atom.

In an alternative embodiment, R$_1$ is selected from the group consisting of

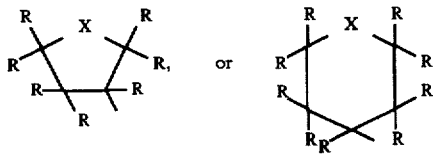

wherein each R may individually selected from the group consisting of H, lower alkyl, and substituted lower alkyl and wherein X is O, or S (—O)$_{0-2}$. In a most preferred embodiment, R$_1$ is selected from the group consisting of 3-tetrahydrofuranyl, 3-tetrahydrothiofuranyl, 4-pyranyl and 4-thiopyranyl.

The following definitions apply to terms as used herein.

The term "halogen" refers to fluorine, bromine, chlorine, and iodine atoms.

The term "oxo" refers to =O.

The term "hydroxyl" refers to the group —OH. The term "lower alkyl" refers to a cyclic, branched or straight chain, alkyl group of one to ten carbon atoms. This term is further exemplified by such groups as methyl, ethyl, n-propyl, i-propyl, n-butyl, t-butyl, i-butyl (or 2-methylpropyl), cyclopropylmethyl, i-amyl, n-amyl, hexyl and the like.

The term "substituted lower alkyl" refers to lower alkyl as just described including one or more groups such as hydroxyl, thiol, allylthiol, halogen, alkoxy, amino, amido, carboxyl, cycloalkyl, substituted cycloalkyl, heterocycle, cycloheteroalkyl, substituted cycloheteroalkyl, acyl, carboxyl, aryl, substituted aryl, aryloxy, hetaryl, substituted hetaryl, aralkyl, heteroaralkyl, alkyl alkenyl, alkyl alkynyl, alkyl cycloalkyl, alkyl cycloheteroalkyl, and cyano. These groups may be attached to any carbon atom of the lower alkyl moiety.

The term "alkoxy" refers to the group —OR, where R is lower alkyl, substituted lower alkyl, acyl, aryl, substituted aryl, aralkyl, substituted aralkyl, heteroalkyl, heteroarylalkyl, cycloalkyl, substituted cycloalkyl, cycloheteroalkyl, or substituted cycloheteroalkyl as defined below.

The term "acyl" denotes groups —C(O)R, where R is hydrogen, lower alkyl substituted lower alkyl, aryl, substituted aryl, amino, and the like as defined below.

The term "aryloxy" denotes groups —OAr, where Ar is an aryl, substituted aryl, heteroaryl, or substituted heteroaryl group as defined below.

The term "amino" refers to the group NR$_2$R$_2$', where R$_2$ and R$_2$' may independently by hydrogen, lower alkyl, substituted lower alky, aryl, substituted aryl, hetaryl, or substituted hetaryl as defined herein.

The term "carboxyl" denotes the group —C(O)OR, where R may independently be hydrogen, lower ally, substituted lower alky, aryl, substituted aryl, hetaryl, substituted hetaryl and the like as defined herein.

The term "aryl" or "Ar" refers to an aromatic carbocyclic group having at least one aromatic ring (e.g., phenyl or biphenyl) or multiple condensed rings in which at least one ring is aromatic, (e.g., 1,2,3,4-tetrahydronaphthyl, naphthyl, anthryl, or phenanthryl).

The term "substituted aryl" refers to aryl optionally substituted with one or more functional groups, e.g., halogen, lower alkyl, lower alkoxy, lower alkylthio, trifluoromethyl, amino, amido, carboxyl, hydroxyl, aryl, aryloxy, heterocycle, hetaryl, substituted hetaryl, nitro, cyano, alkylthio, thiol sulfamido and the like.

The term "heterocycle" refers to a saturated, unsaturated, or aromatic carbocyclic group having a single ring (e.g., morpholino, pyridyl or furyl) or multiple condensed rings (e.g., naphthpyridyl, quinoxalyl, quinolinyl, indolizinyl or benzo[b]thienyl) and having at least one hetero atom, such as N, O or S, within the ring, which can optionally be unsubstituted or substituted with, e.g., halogen, lower alkyl, lower alkoxy, lower alkylthio, trifluoromethyl, amino, amido, carboxyl, hydroxyl, aryl, aryloxy, heterocycle, hetaryl, substituted hetaryl, nitro, cyano, alkylthio, thiol, sulfamido and the like.

The term "heteroaryl" or "hetar" refers to a heterocycle in which at least one heterocyclic ring is aromatic.

The term "substituted heteroaryl" refers to a heterocycle optionally mono or poly substituted with one or more functional groups, e.g., halogen, lower alkyl, lower alkoxy, lower alkylthio, trifluoromethyl, amino, amido, carboxyl, hydroxyl, aryl, aryloxy, heterocycle, hetaryl, substituted hetaryl, nitro, cyano, alkylthio, thiol, sulfamido and the like.

The term "cycloalkyl" refers to a divalent cyclic or polycyclic alkyl group containing 3 to 15 carbon atoms.

The term "substituted cycloalkyl" refers to a cycloalkyl group comprising one or more substituents with, e.g., halogen, lower alyl, substituted lower alkyl, alkoxy, alkylthio, aryl, aryloxy, heterocycle, hetaryl, substituted hetaryl, nitro, cyano, alkylthio, thiol, sulfamido and the like.

The compositions of this invention are useful as A$_1$ receptor agonists for the treatment of cardiac electrical disorders such as supraventricular tachycardias, including atrial fibrillation, atrial flutter, and AV nodal re-entrant tachycardia. The compositions may be administered orally, intravenously, through the epidermis or by any other means known in the art for administering a therapeutic agents.

The method of treatment comprises the administration of an effective quantity of the chosen compound, preferably dispersed in a pharmaceutical carrier. Dosage units of the active ingredient are generally selected from the range of 0.01 to 100 mg/kg, but will be readily determined by one skilled in the art depending upon the route of administration, age and condition of the patient. These dosage units may be administered one to ten times daily for acute or chronic disorders. No unacceptable toxicological effects are expected when compounds of the invention are administered in accordance with the present invention.

If the final compound of this invention contains a basic group, an acid addition salt may be prepared. Acid addition salts of the compounds are prepared in a standard manner in a suitable solvent from the parent compound and an excess of acid, such as hydrochloric, hydrobromic, sulfuric, phosphoric, acetic, maleic, succinic, or methane sulfonic. The hydrochloric salt form is especially useful. If the final compound contains an acidic group, cationic salts may be prepared. Typically the parent compound is treated with an excess of an alkaline reagent, such as hydroxide, carbonate or alkoxide, containing the appropriate cation. Cations such as $Na^+$, $K^+$, $Ca^{+2}$ and $NH_4^+$ are examples of cations present in pharmaceutically acceptable salts. Certain of the compounds form inner salts or zwitterions which may also be acceptable.

Pharmaceutical compositions including the compounds of this invention, and/or derivatives thereof, may be formulated as solutions or lyophilized powders for parenteral administration. Powders may be reconstituted by addition of a suitable diluent or other pharmaceutically acceptable carrier prior to use. If used in liquid form the compositions of this invention are preferably incorporated into a buffered, isotonic, aqueous solution. Examples of suitable diluents are normal isotonic saline solution, standard 5% dextrose in water and buffered sodium or ammonium acetate solution. Such liquid formulations are suitable for parenteral administration, but may also be used for oral administration. It may be desirable to add excipients such as polyvinylpyrrolidinone, gelatin, hydroxy cellulose, acacia, polyethylene glycol, mannitol, sodium chloride, sodium citrate or any other excipient known to one of skill in the art to pharmaceutical compositions including compounds of this invention. Alternatively, the pharmaceutical compounds may be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, teffa alba, magnesium stearate or stearic acid, talc, pectin, acacia, agar or gelatin. The carrier may also include a sustained release material such as glycerol monostearate or glycerol distearate, alone or with a wax. The amount of solid carrier varies but, preferably, will be between about 20 mg to about 1 gram per dosage unit. The pharmaceutical dosages are made using conventional techniques such as milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly or filled into a soft gelatin capsule.

The Examples which follow serve to illustrate this invention. The Examples are intended to in no way limit the scope of this invention, but are provided to show how to make and use the compounds of this invention. In the Examples, all temperatures are in degrees Centigrade.

EXAMPLE 1

The compounds of this invention may be prepared by conventional methods of organic chemistry. The reaction sequence outlined below, is a general method, useful for the preparation of compounds of this invention.

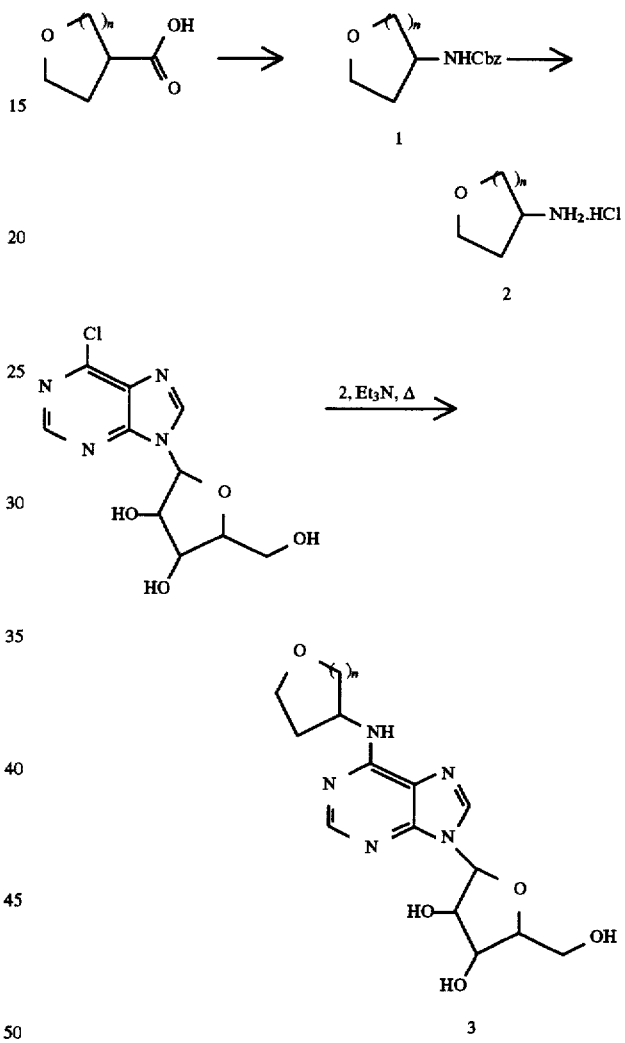

According to this method, oxacycloalkyl carboxylic acid is heated in a mixture of dioxane, diphenylphosphoryazide and triethylamine for 1 hour. To this mixture is added benzyl alcohol and the reaction is further heated over night to give intermediate compound 1. Compound 1 is dissolved in methanol. Next, concentrated HCl, Pd/C is added and the mixture is placed under hydrogen at 1 atm. The mixture is stirred overnight at room temperature and filtered. The residue is recrystallized to give intermediate compound 2. 6-chloropurine riboside is combined and the mixture is compound 2 dissolved in methanol and treated with triethylamine. The reaction is heated to 80° C. for 30 hours. Isolation and purification leads to Compound 3.

EXAMPLE 2

Compounds of this invention prepared according to the method of Example 1 were tested in two functional models specific for adenosine $A_1$ receptor agonist function. The first was the $A_1$ receptor mediated inhibition of isoproterenol stimulated cAMP accumulation in DDT cells. The EC50 of each derivative is shown in Table I. Also shown in Table I is the ability of each derivative to stimulate cAMP production in PC12 cells, a function of agonist stimulation of adenosine $A_2$ receptors. The ratio of the relative potency of each compound in stimulating either an $A_1$ receptor or an $A_2$ receptor effect is termed the selectivity of each compound for the $A_1$ receptor. As can be seen in Table I, each derivative is relatively selective as an $A_1$ receptor agonist. The use of measuring cAMP metabolism as an assay for adenosine $A_1$ receptor function has been previously described (Scammells, P., Baker, S., Belardinelli, L., and Olsson, R., 1994. Substituted 1,3-dipropylxanthines as irreversible antagonists of $A_1$ adenosine receptors. J. Med. Chem 37: 2794-2712, 1994).

TABLE I

| Compound | R | $EC_{50}$ (nM) DDT cells | $EC_{50}$ (nM) PC12 cells | $A_1/A_2$ | $A_2/A_1$ |
| --- | --- | --- | --- | --- | --- |
| I | 4-aminopyran | 12 | 970 | 0.012 | 80.0 |
| II | (±)-3-aminotetrahydrofuran | 13 | 1400 | 0.0093 | 107.6 |
| III | (R)-3-aminotetrahydrofuran | 1.08 | 448 | 0.0024 | 414 |
| IV | (1)-caprolactam | 161 | 181 | 0.889 | 1.12 |
| V | (S)-3-aminotetrahydrofuran | 3.40 | 7680 | 0.00044 | 2258 |

Compounds were also tested in a whole organ model of $A_1$ receptor activation with respect to atrial and AV nodal function. In this model, guinea pig hearts are isolated and perfused with saline containing compound while atrial rate and AV nodal conduction time are assessed by electrographic measurement of atrial cycle length and AV intervals, as detailed in Belardinelli, L, Lu, J. Dennis, D. Martens, J. and Shryock J. (1994); The cardiac effects of a novel A.-adenosine receptor agonist in guinea pig isolated heart. J. Pharm. Exp. Therap. 271:1371-1382 (1994). As shown in FIG. 1, each derivative was effective in slowing the atrial rate and prolonging the AV nodal conduction time of spontaneously beating hearts in a concentration-dependent manner demonstrating efficacy as adenosine $A_1$ receptor agonists in the intact heart.

EXAMPLE 3

Preparation of N-benzyloxycarbonyl-4-aminopyran

A mixture of 4-pyranylcarboxylic acid (2.28 gm, 20 mmol), diphenylphosphorylazide (4.31 ml, 20 mmol), triethylamine (2.78 ml, 20 mmol) in dioxane (40 ml) was heated in a 100° C. oil bath under dry nitrogen for 1 hour. Benzyl alcohol (2.7 ml, 26 mmol) was added, and heating was continued at 100° C. for 22 hours. The mixture was cooled, filtered from a white precipitate and concentrated. The residue was dissolved in 2N HCl and extracted twice with EtOAc. The extracts were washed with water, sodium bicarbonate, brine and then dried over MgSO4, and concentrated to an oil which solidified upon standing. The oil was chromatographed (30% to 60% EtOAc/Hex) to give 1.85 g of a white solid (40%).

Preparation of 4-aminopyran

N-benzyloxycarbonyl-4-aminopyran (1.85 gm, 7.87 mmol) was dissolved in MeOH (50 ml) along with conc. HCl and Pd-C (10%, 300 mg). The vessel was charged with hydrogen at 1 atm and the mixture was allowed to stir for 18 hours at room temperature. The mixture was filtered through a pad of celite and concentrated. The residue was co-evaporated twice with MeOH/EtOAc and recrystallized from MeOH/EtOAc to afford 980 mg (91%) of white needles (mp 228°–230° C.).

Preparation of 6-(4-aminopyran)-purine Riboside

A mixture of 6-chloropurine riboside (0.318 gm, 1. 1 mmol), 4-aminopyran-HCl (0.220 mg, 1.6 mmol) and triethylamine (0.385 ml, 2.5 mmol) in methanol (10 ml) was heated to 80° C. for 30 hours. The mixture was cooled, concentrated and the residue chromatographed (90:10:1, $CH_2Cl_2$/MeOH/$PrNH_2$).

The appropriate fractions were collected and rechromatographed using a chromatotron (2 mm plate, 90:10:1, $CH_2Cl_2$/MeOH/$PrNH_2$) to give an off white foam (0.37 gm, 95%).

EXAMPLE 4

Preparation of N-benzyloxycarbonyl-3-aminotetrahydrofuran

A mixture of 3-tetrahydrofuroic acid (3.5 gm, 30 mmol), diphenylphosphorylazide (6.82 ml, 32 mmol), triethylamine (5 ml, 36 mmol) in dioxane (35 ml) was stirred at RT for 20 min then heated in a 100° C. oil bath under dry nitrogen for 2 hours. Benzyl alcohol (4.7 ml, 45 mmol) was added, and continued heating at 100° C. for 22 hours. The mixture was cooled, filtered from a white precipitate and concentrated. The residue was dissolved in 2N HCl and extracted twice using EtOAc. The extracts were washed with water, sodium bicarbonate, brine dried over MgSO4, and then concentrated to an oil which solidifies upon standing. The oil was chromatographed (30% to 60% EtOAc/Hex) to give 3.4 g of an oil (51%).

Preparation of 3-aminotetrahydrofuran

N-benzyloxycarbonyl-3-aminotetrahydrofuran (3.4 gm, 15 mmol) was dissolved in MeOH (50 ml) along with conc. HCl and Pd-C (10%, 300 mg). The vessel was charged with hydrogen at 1 atm and the mixture was allowed to stir for 18 hours at room temperature. The mixture was filtered through a pad of celite and concentrated. The residue was co-evaporated two times with MeOH/EtOAc and recrystallized from MeOH/EtOAc to give 1.9 g of a yellow solid.

Preparation of 6-(3-aminotetrahydrofuranyl)purine Riboside

A mixture of 6-chloropurine riboside (0.5 gm, 1.74 mmol), 3-aminotetrahydrofuran (0.325 gm, 2.6 mmol) and triethylamine (0.73 ml, 5.22 mmol) in methanol (10 ml) was heated to 80° C. for 40 hours. The mixture was cooled, and concentrated. The residue was filtered through a short column of silica gel eluting with 90/10/1 ($CH_2Cl_2$/MeOH/$PrNH_2$) the fractions containing the product were combined and concentrated. The residue was chromatorgraphed on the chromatotron (2 mm plate, 92.5/7.5/1, $CH_2CL_2$/MeOH/ $P_rNH_2$). The resulting white solid was recrystallized from MeOH/EtOAc to give 0.27 gm of white crystals (mp 128°–130° C.).

EXAMPLE 5

Resolution of 3-aminotetrahydrofuran Hydrochloride

A mixture of 3-aminotetrahydrofuran hydrochloride (0.5 gm, 4 mmol) and (S)-(+)-10-camphorsulfonyl chloride (1.1 gm, 4.4 mmol) in pyridine (10 ml) was stirred for 4 hours at room temperature and then concentrated. The residue was dissolved in EtOAc and washed with 0.5N HCl, sodium bicarbonate and brine. The organic layer was dried over $MgSO_4$, filtered and concentrated to give 1. 17 g of a brown oil (97%) which was chromatographed on silica gel (25% to 70% EtOAc/Hex). The white solid obtained was repeatedly recrystallized from acetone and the crystals and supernatant pooled until an enhancement of greater than 90% by 1H NM was acheived.

Preparation of 3-(S)-aminotetrahydrofuran Hydrochloride

The sulfonamide (170 mg, 0.56 mmol) was dissolved in conc. HCl/AcOH (2 mL each), stirred for 20 hours at room temperature, washed three times with $CH_2Cl_2$ (10 ml) and concentrated to dryness to give 75 mg (qaunt.) of a white solid.

Preparation of 6-(3-(S)-aminotetrahydrofuranyl) purine Riboside

A mixture of 6-chloropurine riboside (30 mg, 0.10 mmol), 3-(S)-aminotetrahydrofuran hydrochloride (19 mg, 0.15 mmol) and triethylamine (45 ml, 0.32 mmol) in methanol (0.5 ml) was heated to 80° C. for 18 hours. The mixture was cooled, concentrated and chromatographed with 95/5 ($CH_2Cl_2$/MeOH) to give 8 mg (24%) of a white solid.

What we claim is:

1. A composition of matter having the formula:

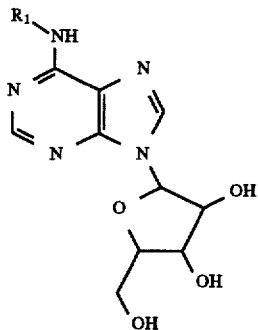

wherein $R_1$ is an unsubstituted or substituted monocyclic heterocyclic group containing from 3 to 15 atoms, at least one of which is selected from the group consisting of N, O, and S(—O)$_{0-2}$ and wherein $R_1$ does not contain an epoxide group.

2. The composition of claim 1 wherein $R_1$ is mono with one or more substituents selected from the group consisting of halogen, oxo, hydroxyl, lower alkyl, substituted lower alkyl, alkoxy, aryl, acyl, aryloxy, carboxyl, substituted aryl, heterocycle, heteroaryl, substituted heteroaryl, cycloalkyl, substituted cycloalkyl, nitro, cyano and mixtures thereof.

3. The composition of matter of claim 1 wherein $R_1$ is a monocyclic, bicyclic, or tricyclic cycloalkyl group containing from 3 to 15 atoms, at least one of which is selected from the group consisting of O or S—(O)$_{0-2}$.

4. The composition of claim 3 wherein $R_1$ is mono or polysubstituted with one or more compounds selected from the group consisting of halogen, oxo, hydroxyl, lower alky, substituted lower alky, alkoxy, aryl, acyl, aryloxy, carboxyl, substituted aryl, heterocycle, heteroaryl, substituted heteroaryl, cycloalkyl, substituted cycloalkyl, nitro, cyano and mixtures thereof.

5. The composition of claim 1 wherein $R_1$ is selected from the group consisting of:

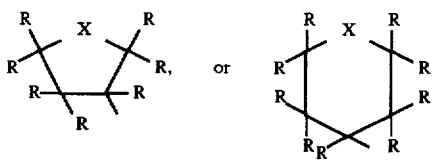

wherein each R may be individually selected from the group consisting of H, lower alkyl, and substituted lower alkyl and wherein X is O, or S (—O)$_{0-2}$.

6. The composition of claim 1 wherein $R_1$ is selected from the group consisting of 3-tetrahydrofuranyl, 3-tetrahydrothiofuranyl, 4-pyranyl, and 4 thiopyranyl.

7. An adenosine type 1 receptor agonist comprising the composition of claim 1.

8. A method for stimulating coronary activity in a mammal experiencing a coronary electrical disorder that can be treated by stimulating an $A_1$ heart adenosine receptor comprising cell proliferation in mammals comprising administering a therapeutically effective amount of the composition of claim 1 to the mammal.

9. The method of claim 8 wherein the therapeutically effective amount ranges from about 0.01 to about 100 mg/kg weight of the mammal.

10. The method of claim 8 wherein the composition is administered to a mammal experiencing a coronary electrical disorder selected from the group consisting of supraventricular tachycardias, atrial fibrillation, atrial flutter, and AV nodal re-entrant tachycardia.

11. The method of claim 10 wherein the mammal is a human.

12. A pharmaceutical composition of matter comprising the composition of claim 1 and one or more pharmaceutical excipients.

13. The pharmaceutical composition of matter of claim 12 wherein the pharmaceutical composition is in the form of a solution.

14. The pharmaceutical composition of matter of claim 13 wherein the pharmaceutical composition is in the form of a tablet.

* * * * *

UNITED STATES PATENT AND TRADEMARK OFFICE
CERTIFICATE OF CORRECTION

PATENT NO. : B1 5,789,416

DATED : October 5, 1999

INVENTOR(S) : Lum et al.

It is certified that error appears in the above-identified patent and that said Letters Patent is hereby corrected as shown below:

On the title page:

At [73] Assignee, delete "Hambrecht & Quist Transition Capatial, LLC, San Francisco, Calif." and replace with -- CV Therapeutics, Inc., Palo Alto, Calif. --

Signed and Sealed this

Eighteenth Day of April, 2000

Attest:

Q. TODD DICKINSON

*Attesting Officer*   *Director of Patents and Trademarks*

REEXAMINATION CERTIFICATE (3894th)

United States Patent [19]
Lum et al.

[11] B1 5,789,416
[45] Certificate Issued Oct. 5, 1999

[54] N⁶ MONO HETEROCYCLIC SUBSTITUTED ADENOSINE DERIVATIVES

[75] Inventors: Robert T. Lum, Palo Alto; Jürg R. Pfister, Los Altos; Steven R. Schow, Redwood City, all of Calif.; Michael M. Wick, Chestnut Hill, Mass.; Marek G. Nelson, Sunol; George F. Schreiner, Los Altos Hills, both of Calif.

[73] Assignee: Hambrecht & Quist Transition Capital, LLC, San Francisco, Calif.

Reexamination Request:
No. 90/005,196, Dec. 16, 1998

Reexamination Certificate for:
Patent No.: 5,789,416
Issued: Aug. 4, 1998
Appl. No.: 08/702,234
Filed: Aug. 27, 1996

[51] Int. Cl.⁶ .................. A61K 31/70; C07D 487/04
[52] U.S. Cl. .................. 514/261; 514/266; 544/262; 544/264
[58] Field of Search ........................ 514/261, 266; 544/262, 264

[56] References Cited

U.S. PATENT DOCUMENTS

| | | | |
|---|---|---|---|
| 3,998,953 | 12/1976 | Konz et al. | 424/253 |
| 4,364,922 | 12/1982 | Berne et al. | 424/9 |
| 4,713,455 | 12/1987 | Furrer et al. | 544/267 |
| 4,954,504 | 9/1990 | Chen et al. | 514/265 |
| 4,980,379 | 12/1990 | Belardinelli et al. | 514/821 |
| 5,288,721 | 2/1994 | Klein et al. | 514/263 |
| 5,446,046 | 8/1995 | Belardinelli et al. | 514/263 |

FOREIGN PATENT DOCUMENTS

| | | |
|---|---|---|
| 0 062 921 | 10/1982 | European Pat. Off. . |
| 0 179 630 A2 | 4/1986 | European Pat. Off. . |
| 0 181 109 A2 | 5/1986 | European Pat. Off. . |
| 0374 808 A2 | 12/1989 | European Pat. Off. . |
| 0 402 752 | 12/1990 | European Pat. Off. . |
| 0 415 456 A2 | 3/1991 | European Pat. Off. . |
| 4205306 A1 | 2/1992 | Germany . |
| WO 88 03148 | 5/1988 | WIPO . |
| WO 90 09178 | 8/1990 | WIPO . |
| WO 92/00297 | 1/1992 | WIPO . |
| WO 93 08206 | 4/1993 | WIPO . |
| WO 94/16702 | 8/1994 | WIPO . |

OTHER PUBLICATIONS

Chemical Abstracts, vol. 105, No. 9, Sep. 1, 1986, abstract No. 106c 72837n.
Chemical Abstracts, vol. 121, No. 3, Jul. 18, 1994, abstract No. 26237z.
L. Belardinelli, *Drug Development Research*, 28, pp. 263–267 (1993).
L. Belardinelli, et al, *Pace*, vol., 14, pp. 1672–1680 (1991).
L. Belardineilli, et al, *Progress in Cardiovascular Disease*, vol. XXXII, No. 1 (Jul./Aug.), pp. 73–97 (1989).
L. Belardinellli, et al, *Cardiac Electrophysiology of Adenosine*, pp. 327–339 (1990).
R. Olsson, et al, *The American Physiological Society*, vol. 70, pp. 761–782 (1990).
R. Olsson, et al, *The American Physiological Society*, vol. 70, pp. 783–805 (1990).
R. Olsson, et al, *The American Physiological Society*, vol. 70, pp. 806–826 (1990).
R. Olsson, et al, *The American Physiological Society*, vol. 70, pp. 827–845 (1990).
Fleysher, *J. Med. Chem*, vol. 15, pp. 187–191 (1972).
K. Jacobsen, et al, *American Chemical Society*, vol. 35, pp. 407–422 (1992).

*Primary Examiner*—Mukund J. Shah

[57] ABSTRACT

A substituted N⁶-oxa, thia, thioxa and azacycloalkyl substituted adenosine derivative and a method for using the composition as an $A_1$ heart adenosine receptor.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 3 is cancelled.

Claim 1 is determined to be patentable as amended.

Claims 2 and 4–14, dependent on an amended claim, are determined to be patentable.

New claim 15 is added and determined to be patentable.

1. A composition of matter having the formula:

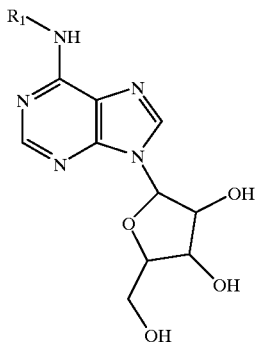

wherein $R_1$ is an unsubstituted or substituted monocyclic heterocyclic group containing from 3 to 15 atoms, at least one of which is selected from the group consisting of N, O, and $S(-O)_{0-2}$ and wherein $R_1$ *is not a monocyclic lactam or imide, and wherein $R_1$ does not contain an epoxide group.*

*15. A composition of matter having the formula:*

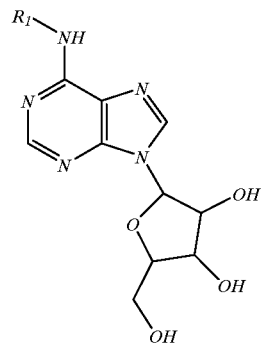

*wherein $R_1$ is a monocyclic, bicyclic, or tricyclic cycloalkyl group containing from 3 to 15 atoms, at least one of which is selected from the group consisting of O, or $S(-O)_{0-2}$.*

* * * * *